US005110942A

United States Patent [19]

Harder et al.

[11] Patent Number: 5,110,942

[45] Date of Patent: May 5, 1992

[54] DYE DERIVED FROM A PYRAZOLOTRIAZOLE

[75] Inventors: John W. Harder; Paul A. Burns, both of Rochester, N.Y.

[73] Assignee: Eastman Kodak Company, Rochester, N.Y.

[21] Appl. No.: 576,031

[22] Filed: Aug. 31, 1990

Related U.S. Application Data

[62] Division of Ser. No. 452,907, Dec. 19, 1989, Pat. No. 4,990,430.

[51] Int. Cl.[5] .......... C07D 487/04

[52] U.S. Cl. .......... 548/262.4

[58] Field of Search .......... 548/262.4

[56] References Cited

U.S. PATENT DOCUMENTS 4,777,121 10/1988 Buckland et al. .......... 430/386

FOREIGN PATENT DOCUMENTS 0284239 9/1988 European Pat. Off. .

0285274 10/1988 European Pat. Off. .

OTHER PUBLICATIONS

Professional Photographer, Nov. 1989, vol. 116, No. 2130, pp. 45-48.

*Primary Examiner*—Mary C. Lee

*Assistant Examiner*—Lenora Miltenberger

*Attorney, Agent, or Firm*—Arthur E. Kluegel

[57] ABSTRACT

A method of retouching a dye image comprises selective removal with an aqueous acidic organic solvent solution, as described in the application, of a portion of a dye image from an exposed and processed photographic silver halide element comprising a support bearing a dye image from a dye-forming coupler and a primary amine photographic color developing agent, wherein the dye-forming coupler: (a) contains so ionizable group that is retained as part of a dye formed upon oxidative coupling, (b) has a structure such that the Log P of the coupler is greater than 4 and is derived from a four-equivalent coupler that has a Log P less than 8, and (c) has a coupling reactivity that enables formation of maximum image density of at least 0.6. The method comprises the step of contacting the dye image with an aqueous acidic organic solvent solution, as described in the application, for a time and at a temperature sufficient to selectively dissolve and remove a portion of the dye image from the photographic element. A new photographic element designed for such retouching comprises new pyrazolotriazole couplers as described in the application.

4 Claims, No Drawings

DYE DERIVED FROM A PYRAZOLOTRIAZOLE

This is a divisional of application Ser. No. 452,907, filed Dec. 19, 1989, now U.S. Pat. No. 4,990,430.

This invention relates to methods and materials for improved retouching of dye images in photographic elements and to new couplers and dyes useful in such methods and materials.

Retouching of dye images in photographic elements and processes has been known in the photographic art. Such retouching typically involves selective removal of a portion of the dye image by means of selective dissolving or destroying a portion of the dye image. Such retouching is described in, for example, trade publications from, for example, Fuji Photo in Japan and Eastman Kodak Company in the United States and in other publications in the photographic art, such as Professional Photographer, Nov. 1989, Vol. 116, No 2130, pages 44 to 48.

A problem that has been encountered with such retouching methods and photographic materials for such retouching has been that a portion of the dye image is not selectively removed without adversely removing or otherwise affecting other portions of the image than that desired to be removed. For example, it has been very difficult to remove a portion, or selectively reduce the dye density, of a magenta dye image without removing a portion of a yellow and/or cyan dye image. This has been an especially difficult problem with selective removal of magenta dye images because it has been difficult to provide magenta dyes from couplers that enable such selective removal.

The present invention solves these problems by providing a method of retouching a dye image comprising selective removal with an aqueous acidic organic solvent solution of an inorganic or organic acid and a water miscible organic solvent of a portion of a dye image from an exposed and processed photographic silver halide element comprising a support bearing a dye image from a dye-forming coupler and a primary amine photographic color developing agent, wherein the dye-forming coupler: (a) contains no ionizable group that is retained as part of a dye formed upon oxidative coupling, (b) has a structure such that the Log P of the coupler is greater than 4 and is derived from a four-equivalent coupler that has a Log P less than 8, and (c) has a coupling reactivity that enables formation of a maximum image density of at least 0.6; wherein the method comprises the step of contacting the dye image with an aqueous acidic organic solvent solution of an inorganic or organic acid and a water miscible organic solvent solution, preferably an aqueous acidic alcohol solution, for a time and at a temperature sufficient to selectively dissolve and remove a portion of the dye image from the photographic element. In the described method the coupler typically is a cyan, magenta or yellow dye-forming coupler.

A preferred photographic element designed to provide a dye image that is retouchable by means of an aqueous acidic organic solvent solution, as described, preferably an aqueous acidic alcohol solution, comprises a support bearing at least one silver halide emulsion layer and associated therewith a magenta dye-forming coupler capable upon oxidative coupling of forming a dye that can be removed from the element by contacting the element with an aqueous acidic organic solvent solution, wherein the coupler is a 6-alkyl, preferably a 6-t-alkyl, 1H-pyrazolo[3,2-c]-1,2,4-triazole coupler having a group in the 3-position that is represented by the formula:

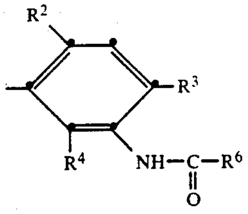

wherein $R^2$, $R^3$ and $R^4$ individually are hydrogen, unsubstituted or substituted alkyl containing 1 to 5 carbon atoms or alkoxy containing 1 to 3 carbon atoms; $R^6$ is

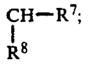

$R^7$ and $R^8$ individually are hydrogen, unsubstituted or substituted alkyl, unsubstituted or substituted phenyl, carbonamido, phenoxy, sulfonamido, sulfamyl, carbamoyl, heterocyclic, hydroxy, phosphoramido, sulfonyl, sulfinyl, or unsubstituted or substituted polyether groups, that enable the coupler to have a Log P, as described, that is within the range of 4 to 8; at least one of $R^7$ and $R^8$ being other than hydrogen. Such a photographic element can also comprise a yellow dye-forming coupler and a cyan dye-forming coupler.

The techniques and steps known in the photographic art for retouching can be used in the described process and with the described photographic element provided that the selective image dye removal is done with an aqueous acidic organic solvent solution of an inorganic or organic acid and a water miscible organic solvent, preferably an acidic alcohol solution, and the photographic element comprises a dye image formed from the described coupler having the required properties, especially a Log P within the range as described, that is within the range of 4 to 8.

The described coupler enables improved selective removal of a dye-image from the element due at least in part to the improved solubility characteristics of the dye in the image areas of the exposed and processed photographic element. The described preferred coupler remains in the layer of the photographic element in which the coupler is incorporated and forms immobile dye upon oxidative coupling with a color developing agent. However, the dye formed is easily removed from the element upon the described retouching when contacted with an aqueous acidic acid organic solvent solution of an inorganic or organic acid and a water miscible organic solvent, preferably an aqueous acidic alcohol solution. The coupler from which the dye is formed contains no ionizable group other than the one responsible for coupling and has a Log P with the range of 4 to 8, as described, which provides the desired solubility.

The Log P herein is the logarithm of the partition coefficient of a species between a standard organic phase, usually octanol, and an aqueous phase, usually water. The color photographic element according to the invention is a polyphasic system and the coupler can partition between the various phases. The Log P indicates the desired level of solubility of the coupler in the phases of the element. Couplers that have a Log P less than 4 and that are derived from a four-equivalent coupler that has a Log P greater than 8 do not have the desired solubility characteristics, that is, for example, they do not provide dyes upon oxidative coupling that are selectively removed in the retouching process to a desired degree or are too soluble to remain in a desired location in a photographic element as described. The four-equivalent coupler, as described, is a coupler that does not contain a coupling-off group in the coupling position. The term "four-equivalent" is as used in the photographic art. The calculated Log P (c Log P) herein means the Log P value provided by calculating the Log P as described without the presence of the coupling-off group of the coupler. For instance, for following compound No. 1 in Example 1, the c Log P is 6.4 and calculated for the coupler without the presence of the $Z^1$, that is without chlorine in the coupling position.

The Log P values herein are calculated by the methods and compositions described in U.S. Pat. No. 4,782,012, the description of which is incorporated herein by reference.

The cyan, magenta and yellow couplers having the described properties in a photographic element that is retouchable by means of an aqueous acidic acid organic solvent solution of an inorganic or organic acid and a water miscible organic solvent, preferably an acidic alcohol solution, as described, can be selected from such couplers known in the photographic art. Any cyan, magenta, or yellow coupler is useful that has the described properties, especially a Log P within the range as described.

Typical examples of such couplers and the c Log P for such couplers are as follows:

| Coupler: | c Log P |
| --- | --- |
| YELLOW: | |
| 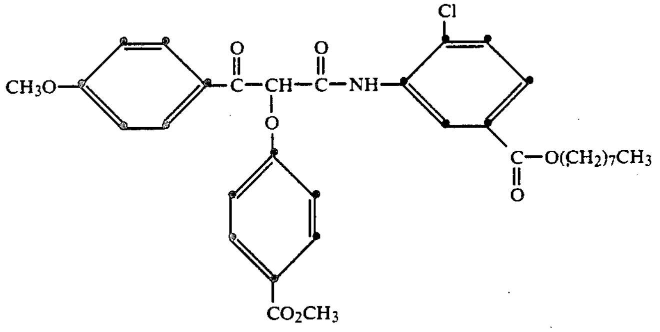 | 7.7 |
| 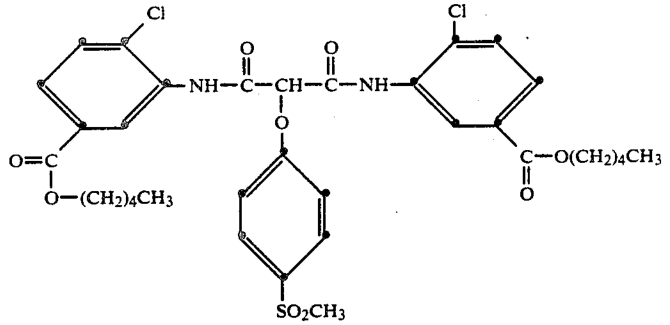 | 7.3 |
| 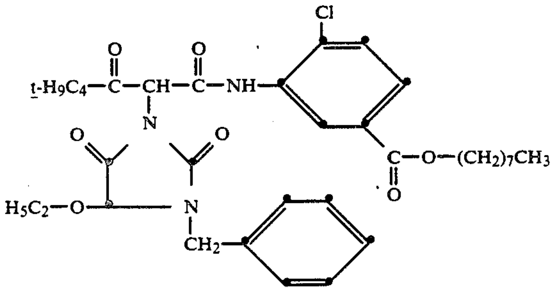 | 6.2 |

-continued
| Coupler: | c Log P |
|---|---|
| 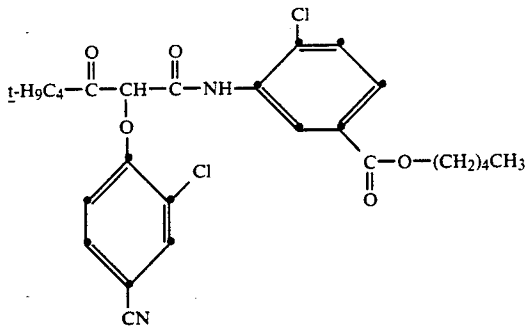 | 5.2 |
| 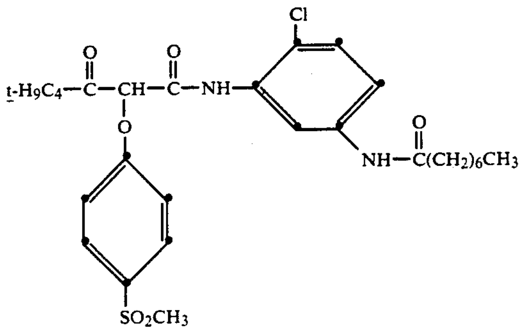 | 5.5 |
| MAGENTA: | |
| 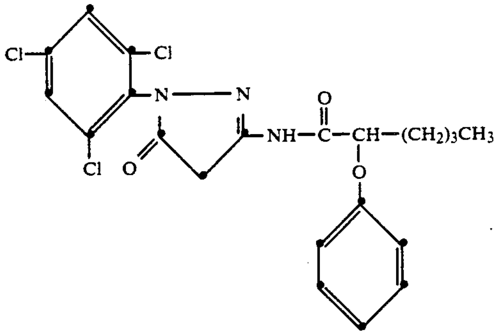 | 6.8 |
| 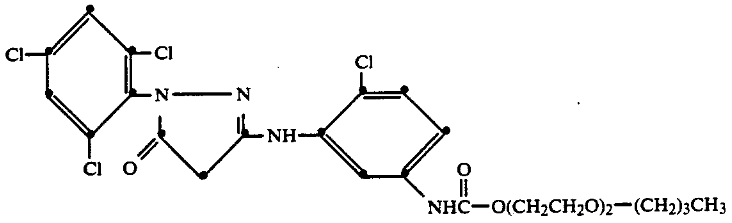 | 7.9 |
| 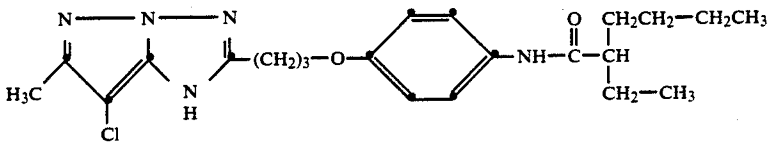 | 6.7 |

-continued

| Coupler: | c Log P |
| --- | --- |
| 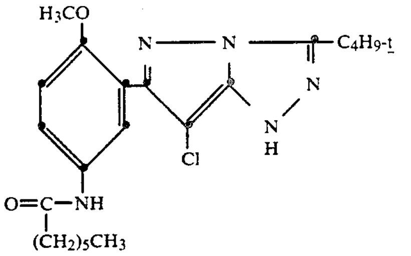 | 6.0 |
| 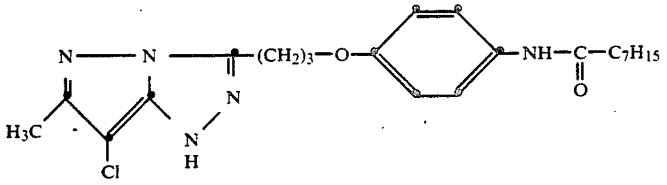 | 6.0 |
| CYAN: | |
| 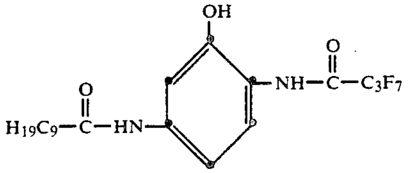 | 6.7 |
| 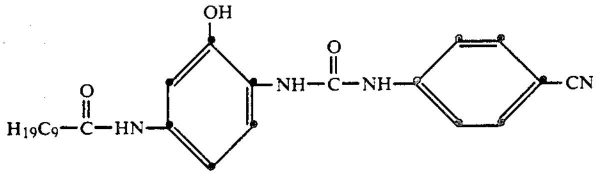 | 5.8 |
| 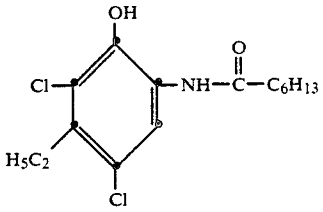 | 6.1 |
| 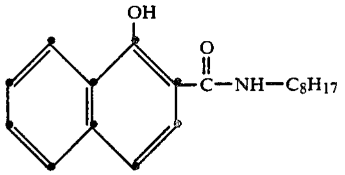 | 6.0 |
| 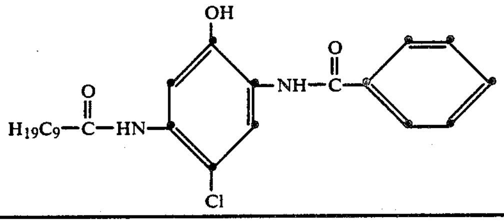 | 5.6 |

Useful couplers have sufficient reactivity to enable the coupler upon oxidative coupling with a color developing agent as described to form a dye image having a maximum image density of at least 0.6. The method of measuring such reactivity is by means of a conventional exposure and development process in which the coupler is incorporated in conventional photographic element and the element is then imagewise exposed and processed using a conventional color developer to provide a dye image. The density of the resulting dye image is measured to determine the maximum image density. A typical element and process for such purposes is described in following Example 1.

A preferred coupler is a pyrozolotriazole magenta dye-forming coupler represented by the formula:

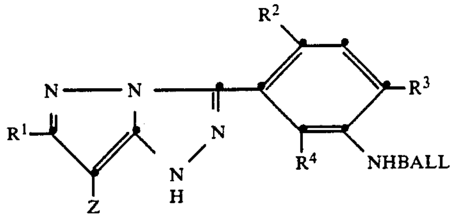

wherein $R^1$ is an unsubstituted or substituted alkyl or aryl group that does not adversely affect the desired properties of the coupler, preferably an unsubstituted or substituted secondary or tertiary alkyl group, such as one containing 1 to 5 carbon atoms, for example, i-propyl or t-butyl, with t-butyl being highly preferred;

Z is hydrogen or a coupling-off group known in the photographic art, such as halogen, particularly chlorine or phenoxy coupling-off groups;

$R^2$, $R^3$ and $R^4$ individually are hydrogen; unsubstituted or substituted alkyl groups, such as alkyl containing 1 to 5 carbon atoms, for example, methyl, ethyl, propyl or butyl; or unsubstituted or substituted alkoxy, such as alkoxy containing 1 to 3 carbon atoms, for example methoxy or ethoxy; and, BALL is a ballast group that enables the coupler to have a Log P, within the described range, that is within the range of 4 to 8, as described.

The ballast group (BALL) as described is an organic radical of such size and configuration that confers on the coupler molecule sufficient bulk to render the coupler substantially non-diffusible from the layer in which it is coated in the photographic element. The ballast also confers upon the coupler the solubility characteristics that enable the coupler to have a Log P within the described range of 4 to 8. Any ballast group is useful that provides the described characteristics. A typical ballast group is a carbonamido ballast group, such as $-NHCOR^5$ as described.

The coupling-off group as described can be any coupling-off group known in the photographic art. Examples of useful coupling-off groups are described in, for instance, U.S. Pat. No. 4,849,328. Preferred coupling-off groups are chlorine and phenoxy coupling-off groups.

A method of forming an image in an exposed photographic element containing the described couplers comprises developing the exposed element by means of a color developing agent with formation of a dye in the image areas that is retouchable using an acidic alcohol solution. The color developing agent can be any color developing agent known in the photographic art that can provide such a dye image upon oxidative coupling, preferably a primary amine photographic color developing agent. Examples of such preferred color developing agents are: 4-amino-N,N-diethylaniline hydrochloride; 4-amino-3-methyl-N,N-diethylaniline hydrochloride; 4-amino-3-methyl-N-ethyl-N-β-(methanesulfonamido)-ethylaniline sulfate hydrate; 4-amino-3-methyl-N-ethyl-N-β-hydroxyethylaniline sulfate; 4-amino-3-β-(methanesulfonamido)-ethyl-N,N-diethylaniline hydrochloride; or, 4-amino-N-ethyl-N-(2-methoxyethyl)-m-toluidine di-p -toluenesulfonic acid.

A typical method of forming an image in an exposed color photographic silver halide element comprising cyan, magenta and yellow couplers as described comprises developing a dye image in the photographic element with a color developing agent as described and, after processing the element, selective removal of at least a portion of the dye image with an aqueous acidic organic solvent solution of an inorganic or organic acid and a water miscible organic solvent, preferably an acidic alcohol solution, as described. This method preferably comprises selective removal with an acidic alcohol solution of at least a portion of a magenta dye image formed from a magenta coupler as described without removal of cyan and yellow dye images.

The aqueous acidic organic solvent solution of an inorganic or organic acid and a water miscible organic solvent, preferably an acidic alcohol solution, that is useful in the described process can be any acidic alcohol solution that enables the selective removal of at least a portion of the dye image as described. The solution, as described, comprises a solution of an inorganic or organic acid, such as an acid selected from the following inorganic or organic acids: hydrochloric, phosphoric, nitric, sulfuric, hydrofluoric, alkyl or aryl sulfonic acids, alkyl or aryl carboxylic acids, alkyl or aryl phosphorus acids.

The water miscible organic solvent is typically selected from the following: 3A alcohol (95% ethanol, 5% methanol), methanol, ethyleneglycol, polyethyleneglycol, ethanol, isopropanol, propanol; also organic solvents such as tetrahydrofuran, acetone, dimethylformamide, dimethylsulfoxide, dimethylacetamide, pyrrolidinone and sulfolane. Ethanol is preferred.

The ratio of aqueous acid to organic solvent in the acidic solvent solution as described is typically within the range that provides an acidity that is $10^{-7}$ to $10^{1}$ molar in acid with typical values of $10^{-1}$ to $10^{-4}$ molar. The organic solvent, for example alcohol, to water in the solvent solution ratios are within the range of 4:1 to 1:1 by volume.

The process is typically carried out under ambient conditions of temperature and pressure, preferably under atmospheric conditions, such as about 18° to 25° C.

The optimum time required for carrying out the process of removal of a portion of the dye image as described will depend upon such factors as the particular element, the particular dye image, temperature during the process, particular acidic alcohol solution and the desired final dye image. These can be adjusted according to the desired results. The process of the invention enables a shorter time for retouching than otherwise might be required. The process of the invention can be carried out, for example, within a few minutes rather than more than an hour.

In a preferred photographic element after processing comprises a dye image, that is retouchable as described, and comprises a dye represented by the formula:

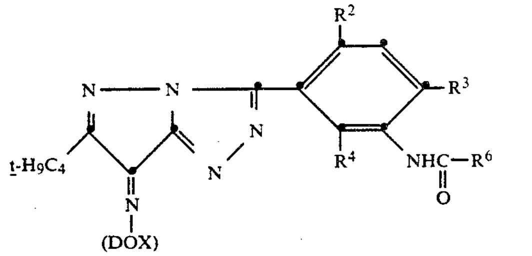

wherein $R^2$, $R^3$, $R^4$ and $R^6$ are as defined and (DOX) is a moiety derived from an oxidized primary amine photographic color developing agent, also as described.

A typical dye that has the described properties in a photographic element is represented by the formula:

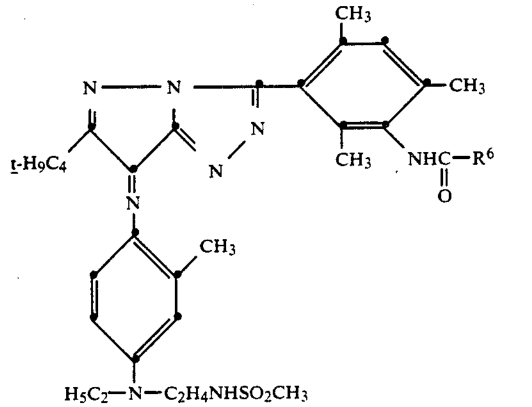

wherein $R^6$ is as defined.

The photographic couplers as described can be incorporated in photographic elements in ways, by means, and in locations that are known in the photographic art.

Photographic elements of the invention can be processed prior to retouching by conventional techniques in which color forming couplers and color developing agents are incorporated in separate processing solutions or compositions or in elements.

Photographic elements in which the compounds of this invention are incorporated can be a simple element comprising a support and a single silver halide emulsion layer or they can be multilayer, multicolor elements. The compounds of this invention can be incorporated in at least one of the silver halide emulsion layers and/or in at least one other layer, such as an adjacent layer, where they will come into reactive association with oxidized color developing agent which has developed silver halide in the emulsion layer. The silver halide emulsion layer can contain or have associated with it, other photographic coupler compounds, such as dye-forming photographic coupler compounds, such as dye-forming couplers. These other photographic couplers can form dyes of the same or different color and hue as the photographic couplers of this invention. Additionally, the silver halide emulsion layers and other layers of the photographic element can contain addenda conventionally contained in such layers.

A typical multilayer, multicolor photographic element can comprise a support having thereon a red-sensitive silver halide emulsion unit having associated therewith a cyan dye image-providing material, a green-sensitive silver halide emulsion unit having associated therewith a magenta dye image-providing material and a blue-sensitive silver halide emulsion unit having associated therewith a yellow dye image-providing material, at least one of the silver halide emulsion units having associated therewith a photographic coupler of the invention. Each silver halide emulsion unit can be composed of one or more layers and the various units and layers can be arranged in different locations with respect to one another.

The couplers of this invention can be incorporated in or associated with one or more layers or units of the photographic element.

The light sensitive silver halide emulsions can include coarse, regular or fine grain silver halide crystals or mixtures thereof and can be comprised of such silver halides as silver chloride, silver bromide, silver bromoiodide, silver chlorobromide, silver chloroiodide, silver chlorobromoiodide and mixtures thereof. The emulsions can be negative-working or direct-positive emulsions. They can form latent images predominantly on the surface of the silver halide grains or predominantly on the interior of the silver halide grains. They can be chemically and spectrally sensitized. The emulsions typically will be gelatin emulsions although other hydrophilic colloids are useful. Tabular grain light sensitive silver halides are particularly useful such as described in *Research Disclosure*, January 1983, Item No. 22534 and U.S. Pat. No. 4,434,226.

The support can be any support used with photographic elements. Typical supports include cellulose nitrate film, cellulose acetate film, polyvinylacetal film, polyethylene terephthalate film, polycarbonate film and related films or resinous materials as well as glass, paper, metal and the like. Typically, a flexible support is employed, such as a polymeric film or paper support. Paper supports can be acetylated or coated with baryta and/or an α-olefin polymer, particularly a polymer of an α-olefin containing 2 to 10 carbon atoms such as polyethylene, polypropylene, ethylene-butene copolymers and the like.

In the following discussion of suitable materials for use in the emulsions and elements of this invention, reference will be made to *Research Disclosure*, December 1978, Item 17643, published by Industrial Opportunities Ltd., Homewell Havant, Hampshire, PO9 1EF, U.K., the disclosures of which are incorporated herein by reference. This publication will be identified hereafter by the term "Research Disclosure".

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Development of an image with a color developing agent as described is typically followed by conventional steps of bleaching, fixing, or bleach-fixing, to remove silver and silver halide, washing and drying.

Couplers as described can be prepared by reactions and methods known in the photographic art. The following illustrate methods of synthesis of a pyrazolotriazole coupler of the invention:

Synthesis A

Synthesis Example A

The 1-acetyl-6-t-butyl-7-chloro-(3-amino-2,4,6-trimethylphenyl)-1H-pyrazolo[3,2-c]-1,2,4-triazole (Compound C) was prepared as described in U.S. Pat. No. 4,777,121 and reacted with an acid chloride as described in the following reactions:

Bis(hydroxymethyl)propionic acid (50 g, 0.37 mol) was treated with acetic anhydride (150 ml) and pyridine (50 ml) and stirred at room temperature (20° C.) for 24 hours. The reaction mixture was concentrated to dryness at <80° C. The oily residue crystallized on standing and was recrystallized from $CCl_4$ to give 35 g of bis(acetoxymethyl)propionic acid. 5.8 g (0.03 mol) of bis(acetoxymethyl)propionic was dissolved in 50 ml dichloromethane and treated with 3 ml oxalyl chloride and 2 drops of dimethylformamide. The solution was stirred at room temperature under $N_2$ for three hours and concentrated.

Preparation of Compound A:

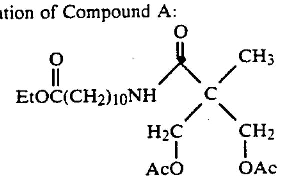

Compound A

The bis(acetoxymethyl)proprionyl chloride (0.03 mol) was dissolved in 15 ml of tetrahydrofuran and added dropwise to a mixture of ethyl 11-aminoundecanoate hydrochloride salt (8 g, 0.03 mol) and triethylamine (6.1 g, 0.06 mol) and stirred at room temperature for 24 hours. The reaction mixture was filtered and the filtrate was partitioned between ethyl acetate and 10% HCl. The organic layer was dried and concentrated to yield 12 g of Compound A. (Ac herein means acetate.) (Et herein means ethyl.)

Compound A

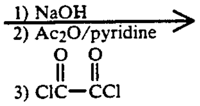

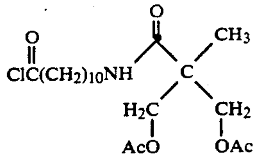

Compound B

Compound A (9 g, 0.02 mol) was dissolved in tetrahydrofuran (200 ml) and treated with 50% aqueous NaOH (8 g, 0.10 mol) and enough $H_2O$ to make the solution cloudy. The reaction solution was stirred for 24 hours at room temperature, acidified with 10% HCl and partitioned with ethyl acetate. The organic layer was dried ($MgSO_4$) and concentrated. The residue was dissolved in pyridine (100 ml), treated with acetic anhydride (6.2 g, 0.06 mol), stirred at room temperature for 4 hours. The mixture was poured into ice and concentrated HCl and extracted with ethyl acetate. The organic layer was washed with 10% HCl, dried ($MgSO_4$) and concentrated. The residue was dissolved in $CH_2Cl_2$ and treated with oxalyl chloride (3 ml, 0.035 mol) and 2 drops of dimethylformamide. The solution was stirred for 3 hours, and then the solution of Compound B was concentrated and used immediately.

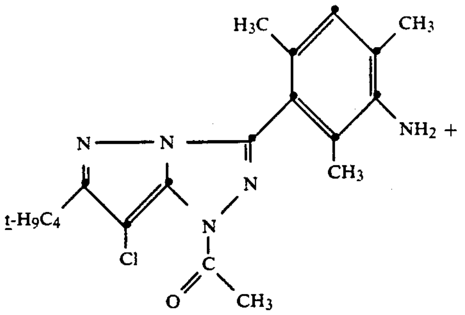

Compound C

Compound B

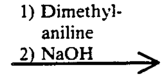

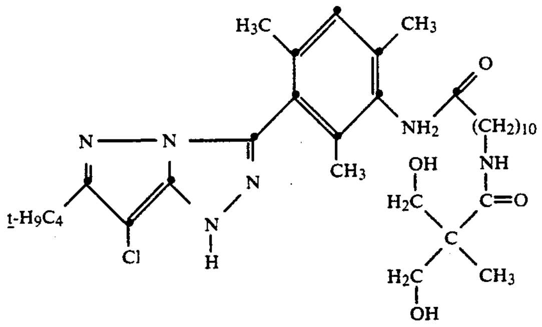

Compound D

Compound C (8 g, 0.02 mol) was dissolved in tetrahydrofuran (200 ml) and N,N-dimethylaniline (3 g) and treated with a solution of Compound B (8.8 g, 0.02 mol) in tetrahydrofuran (20 ml) dropwise at room temperature. The solution was stirred for one hour at room temperature and partitioned between ethyl acetate and 10% HCl. The organic layer was dried ($MgSO_4$) and concentrated. The residue was dissolved in tetrahydrofuran (50 ml) and methanol (50 ml) and treated with 50% aqueous NaOH (8 g, 0.1 mol) and stirred at room temperature for one hour. The reaction solution was partitioned with ethyl acetate and 10% HCl, and the organic layer was dried ($MgSO_4$) and concentrated. The residue was chromatographed on silica gel eluted with ethyl acetate and dichloromethane to give Compound D of the invention. The structure was consistent with the NMR and analysis data.

Synthesis Example B

Methyl 6-bromohexanoate (21 g, 0.1 mol), p-hydroxybenzaldehyde (12.2 g, 0.1 mol), and sodium methoxide (5.4 g, 0.1 mol) were dissolved in methanol (200 ml) and heated at reflux for 24 hours. The reaction mixture was partitioned with ethyl acetate and $H_2O$ and the organic layer was dried ($MgSO_4$) and concentrated. The residue (Compound E) was carried on to the next reaction.

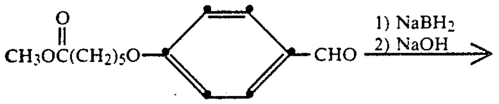

Compound E

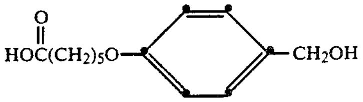

Compound F

Compound E (22 g, 0.09 mol) was dissolved in methanol (100 ml) and treated with sodium borohydride (8 g, 0.2 mol) in small portions. The solution was stirred for 4 hours and poured into a mixture of 10% HCl and ice. The product was partitioned into ethyl acetate, and the organic layer was dried ($MgSO_4$) and concentrated. The residue was dissolved in tetrahydrofuran and treated with 50% aqueous NaOH (10 g, 0.12 mol) and enough $H_2O$ to make the solution turbid. The reaction solution was stirred for 2 hours at room temperature, acidified with 10% HCl, and partitioned with ethyl acetate. The organic layer was dried ($MgSO_4$) and concentrated to an oil (Compound F) which was carried on to the next reaction.

Compound F 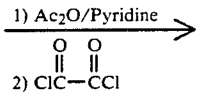

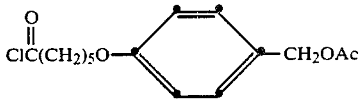

Compound G

Compound F (12 g, 0.05 mol) was dissolved in 50 ml pyridine and treated with acetic anhydride (10 g, 0.1 mol) and the solution stirred at room temperature for 4 hours. The solution was poured onto ice and concentrated hydrochloric acid and stirred for 10 minutes. The mixture was partitioned with ethyl acetate, and the organic layer was dried ($MgSO_4$) and concentrated. The residue was dissolved in dichloromethane and treated with oxalyl chloride (5 ml, 0.06 mol) and the solution stirred at room temperature for 3 hours. The solution was evaporated to give Compound G.

Compound C + Compound G 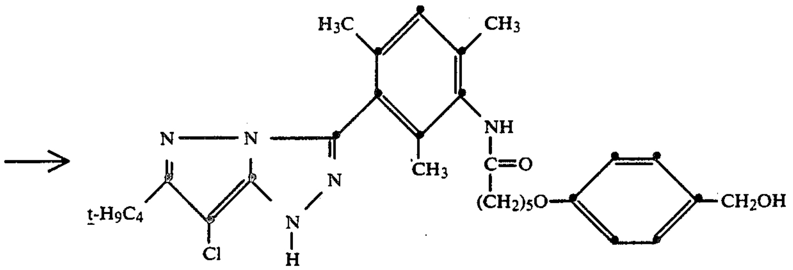

Compound H

Compound C (8 g, 0.02 mol) was dissolved in tetrahydrofuran and N,N-dimethylaniline (2.5 g, 0.02 mol) and treated with a solution of Compound G (6 g, 0.02 mol) in tetrahydrofuran (20 ml). The solution was stirred for one hour at room temperature and partitioned with ethyl acetate and 10% HCl. The organic layer was dried over $MgSO_4$ and concentrated. The residue was dissolved in tetrahydrofuran (50 ml) and methanol (50 ml) and treated with 50% aqueous NaOH (4 g, .05 mol) and stirred at room temperature for 2 hours. The reaction mixture was partitioned with ethyl acetate and 10% HCl, and the organic layer was dried and concentrated. The residue was chromatographed on silica gel eluted with ethyl acetate and dichloromethane to give the desired Compound H whose structure was consistent with the NMR and analytical data.

The following examples further illustrate the invention.

EXAMPLES 1-24

Photographic elements were prepared by coating a cellulose acetatebutyrate film support with a photosensitive layer containing a silver bromoiodide emulsion at 0.84 g Ag/sq m, gelatin at 3.77 g/sq m, and one of the couplers designated in Table I dispersed in half its weight of tricresylphosphate and coated at 1.62 mmol/sq m. The photosensitive layer was overcoated with a layer containing gelatin at 7.0 g/sq m and bis-vinylsulfonylmethyl ether at 1.75 weight percent based on total gelatin. Samples of each element were image-wise exposed through a graduated-density test object and processed at 40° C. employing the processing steps and processing solutions of the Kodak E-6 process of Eastman Kodak Co., U.S.A (Kodak is a trademark of Eastman Kodak Co., U.S.A.), as described in, for example, *The British Journal of Photography*, 1982 Annual, pages 201-203.

| Processing Steps | Time | Temperature |
|---|---|---|
| First Development | 3 | 38 |
| Wash | 2 | 38 |
| Reversal | 2 | 38 |
| Color Development | 6 | 38 |
| Conditioner | 2 | 38 |
| Bleach | 6 | 38 |
| Fixer | 4 | 38 |
| Final Wash | 4 | 38 |
| Stabilizer | 0.5 | 38 |

The produced magenta dye images were evaluated by several tests and measurements as shown in Table II. Densitometry of these images provided measures of maximum density ($D_{max}$) and change in density (wash-out density) caused by immersing the dye image in a stirred solution of 3 ml of 12N HCl, 32 ml of $H_2O$ and 65 ml of ethanol for 3 minutes.

The c Log P values used in these examples were calculated using the additive fragment techniques of C.

Hansch and A. Leo as described in *Substituent Constants for Correlation Analysis in Chemistry and Biology*, Wiley, N.Y., 1979, using the computer program "MedChem", version 3.53, Medicinal Chemistry Project, Pomona College, Claremont, CA (1984) as described in U.S. Pat. 4,782,012. The c Log P values are calculated for the four equivalent coupler since the coupling-off group is not present in the resulting dye molecule.

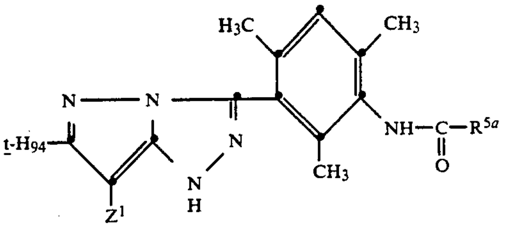

TABLE I

| Compound and Example | $R^{5a}$ | $Z^1$ | c Log P* |
|---|---|---|---|
| 1 | $-(CH_2)_{10}NH\overset{\overset{O}{\|}}{P}(OEt)_2$ | Cl | 6.4 |
| 2 | $-(CH_2)_{10}SO_2(CH_2)_2NHSO_2C_3H_7$ | Cl | 6.3 |
| 3 | $-(CH_2)_{10}SO_2(CH_2)_2NH\overset{\overset{O}{\|}}{P}(OEt)_2$ | Cl | 6.1 |
| 4 | $-(CH_2)_{10}NH\overset{\overset{O}{\|}}{C}C(CH_3)(CH_2OH)_2$ | Cl | 5.3 |

TABLE I-continued

| Compound and Example | $R^{5a}$ | $Z^1$ | c Log P* |
|---|---|---|---|
| 5 | 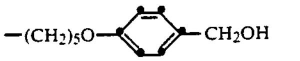 | Cl | 5.2 |
| 6 | 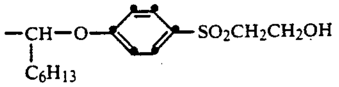 | Cl | 6.0 |
| 7 | 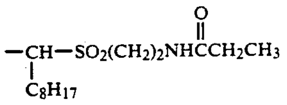 | Cl | 6.3 |
| 8 | 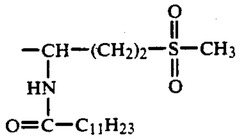 | Cl | 5.8 |
| 9 | 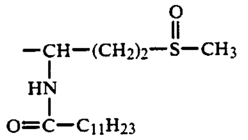 | Cl | 5.8 |
| 10 | 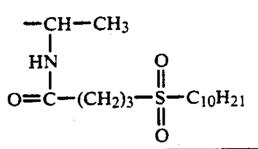 | Cl | 5.88 |

*Calculated for structure wherein $Z^1$ is H.

Comparative Couplers

C-1

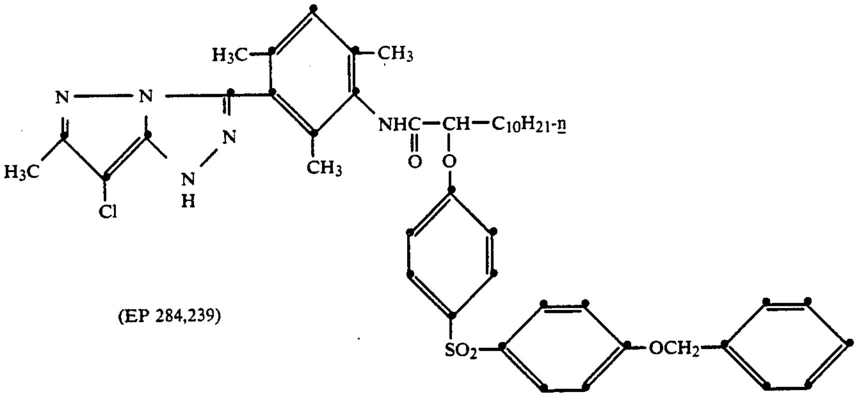

(EP 284,239)

C-2

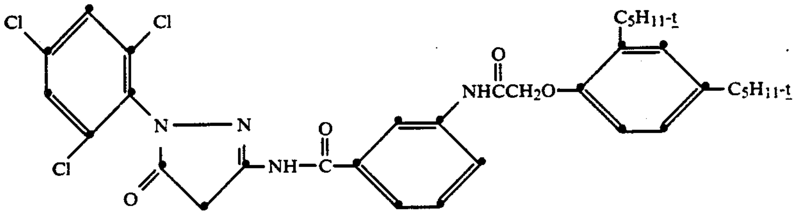

-continued

Comparative Couplers

C-3

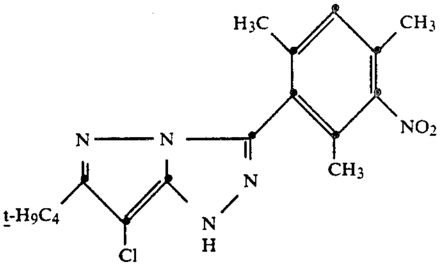

(U.S. Pat. No. 4,777,121)

The following results were obtained using the couplers from Table I:

TABLE II

| Compound and Example No. | $D_{max}$ | Percent Washout | c Log P* |
|---|---|---|---|
| 1 | 0.83 | 54% | 6.4 |
| 2 | 1.74 | 86% | 6.3 |
| 3 | 1.06 | 94% | 6.1 |
| 4 | 1.35 | 89% | 5.3 |
| 5 | 1.10 | 96% | 5.2 |
| 6 | 1.10 | 48% | 6.0 |
| 7 | 0.9 | 81% | 6.3 |

TABLE II-continued

| Compound and Example No. | $D_{max}$ | Percent Washout | c Log P* |
|---|---|---|---|
| C-1 (Comparison) | 0.7 | 3% | 11.0 |
| C-2 (Comparison) | 1.6 | 8% | 10.5 |
| C-3 (Comparison) | 0.5 | 98% | 5.8 |

*Calculated for structure wherein $Z^1$ is H.

The following couplers also can provide useful results using the procedure of Example 1:

| Example | | c Log P* |
|---|---|---|
| 11. | 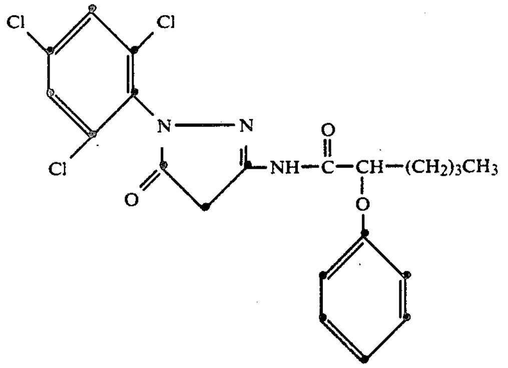 | 6.8 |
| 12. | 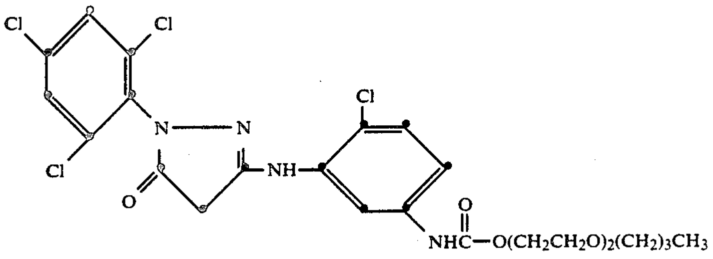 | 7.9 |

-continued
| Example | | c Log P* |
|---|---|---|
| 13. | 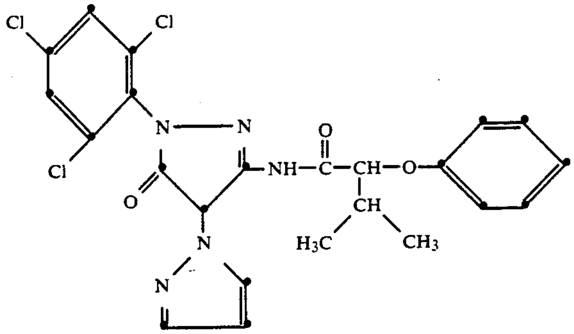 | 6.2 |
| 14. | 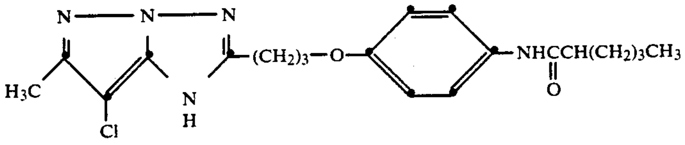 | 6.0 |
| 15. | 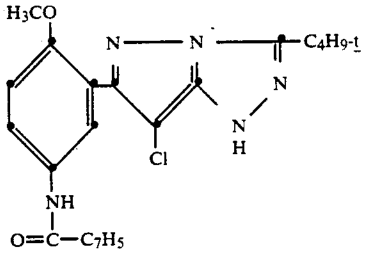 | 5.7 |
| 16. | 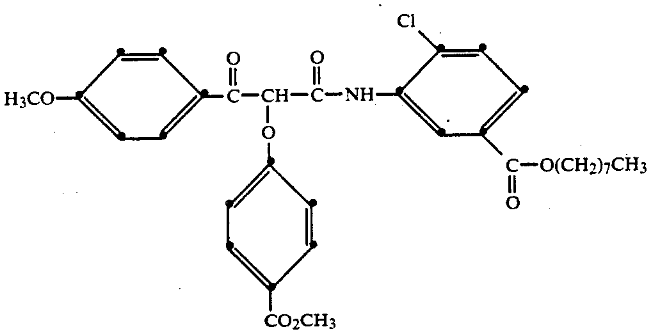 | 7.7 |
| 18. | 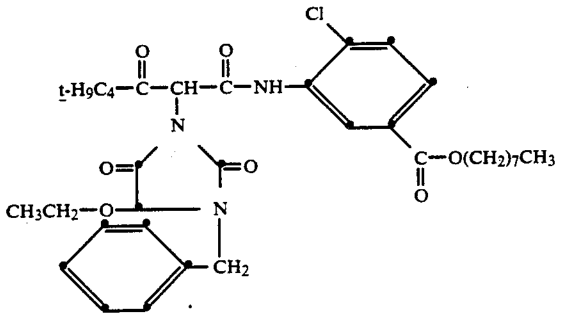 | 6.2 |

-continued
| Example | | c Log P* |
|---|---|---|
| 19. | 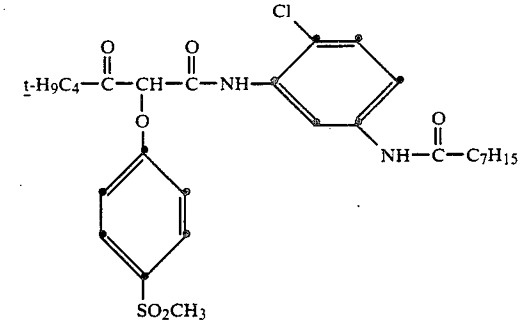 | 5.5 |
| 20. | 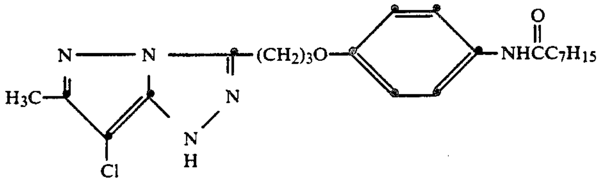 | 5.0 |
| 21. | 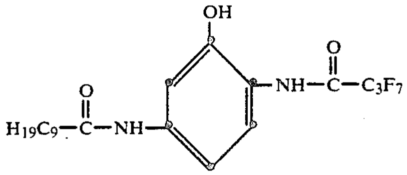 | 6.7 |
| 22. | 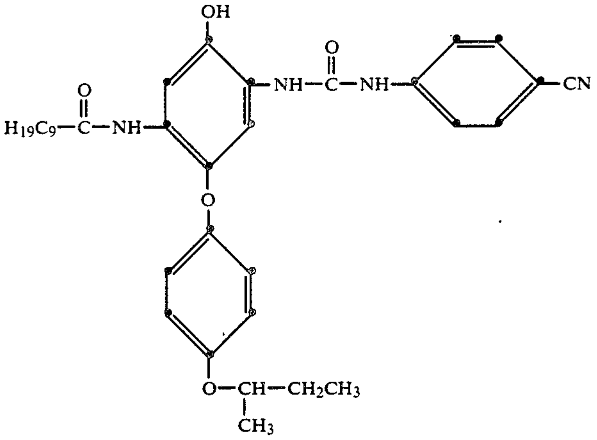 | 5.8 |
| 23. | 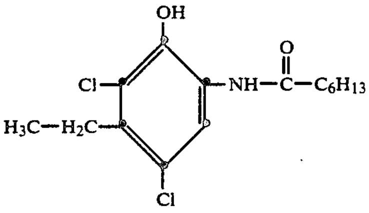 | 5.4 |
| 24. | 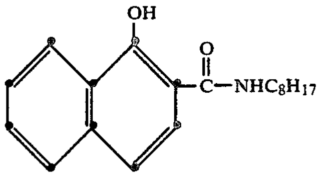 | 6.04 |
*Calculated for structure with H in the coupling position.
The invention has been described in detail with particular reference to preferred embodiments thereof, but

What is claimed is:

1. A dye that is formed upon oxidative coupling of a 6-t-alkyl-1H-pyrazolo-1, 2, 4-triazole photographic coupler having a group in the 3-position represented by the formula:

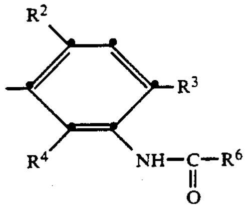

wherein $R^2$, $R^3$ and $R^4$ individually are hydrogen, unsubstituted or substituted alkoxy or unsubstituted or substituted alkyl containing 1 to 5 carbon atoms;

$R^6$ is 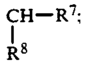

$R^7$ and $R^8$ individually are hydrogen, unsubstituted or substituted alkyl, aryl, carbonamido, phenoxy, sulfonamido, sulfanyl, carbamoyl, hydroxy, phosphoramido, sulfonyl, sulfinyl, or unsubstituted or substituted polyether groups, that enable the coupler to have a Log P that is within the range of 4 to 8; at least one of $R^7$ and $R^8$ is other than hydrogen; and, a primary amine photographic color developing agent.

2. A dye as in claim 1 represented by the formula:

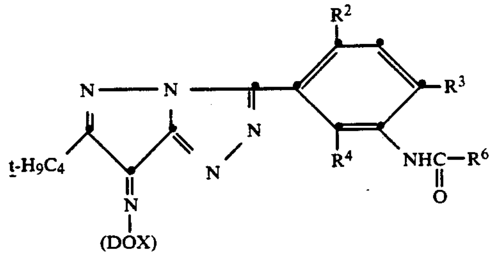

wherein $R^2$, $R^3$, $R^4$ and $R^6$ are as defined in claim 1 and (DOX) is a moiety derived from an oxidized primary amine photographic color developing agent.

3. A dye as in claim 1 represented by the formula:

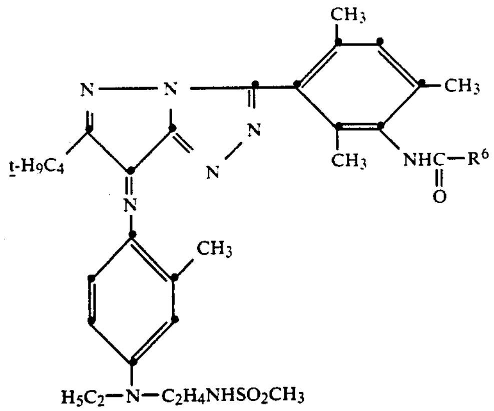

wherein $R^6$ is as defined in claim 1.

4. A dye that is

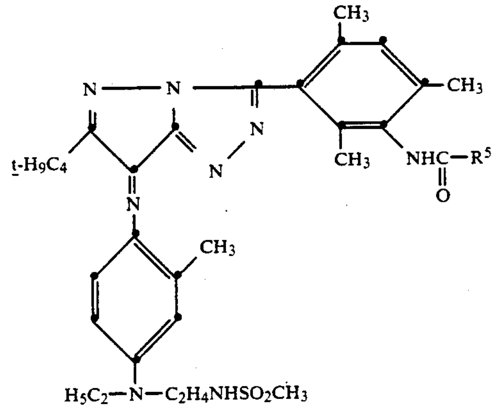

wherein $R^5$ is

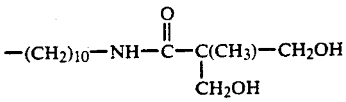

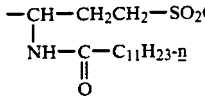

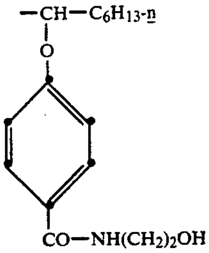

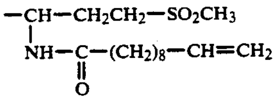

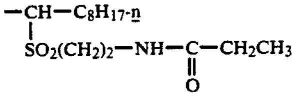

or

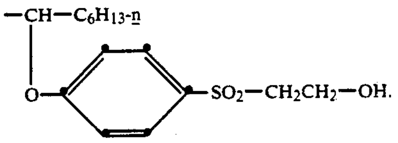

* * * * *